United States Patent [19]

v.d. Vlekkert et al.

[11] Patent Number: 4,691,167
[45] Date of Patent: Sep. 1, 1987

[54] APPARATUS FOR DETERMINING THE ACTIVITY OF AN ION (PION) IN A LIQUID

[75] Inventors: Hendrik H. v.d. Vlekkert, Groningen, Netherlands; Nicolaas F. de Rooy, Bole, Switzerland

[73] Assignee: Sentron v.o.f., Roden, Netherlands

[21] Appl. No.: 642,126

[22] Filed: Aug. 17, 1984

[30] Foreign Application Priority Data

Aug. 24, 1984 [NL] Netherlands .................. 8302964

[51] Int. Cl.[4] .......................................... G01N 27/26
[52] U.S. Cl. ................................. 324/438; 324/715; 324/441; 204/406; 204/416
[58] Field of Search ............... 324/425, 438, 441, 459, 324/62, 71.6, 71.5; 204/406, 416; 357/25; 364/497, 555

[56] References Cited

U.S. PATENT DOCUMENTS

| 4,267,504 | 5/1981 | Bergveld | 324/62 |
| 4,302,299 | 11/1981 | Ishikawa | 364/497 |
| 4,385,274 | 5/1983 | Shimada | 324/438 |

FOREIGN PATENT DOCUMENTS 3144459 10/1982 Fed. Rep. of Germany .
2077439 12/1981 United Kingdom .

OTHER PUBLICATIONS

Electrochemistry of Chemically Sensitive FET's Janata Sensors and Actuators, vol. 4-1983.
P. Bergveld and N. F. de Rooij, "The History of Chemically Sensitive Semiconductor Devices", Sensors and Actuators, (1981), pp. 5-16, printed by Elsevier Sequoia S. A. Lausanne, the Netherlands.

Primary Examiner—Reinhard J. Eisenzopf
Assistant Examiner—Jack B. Harvey
Attorney, Agent, or Firm—Henry W. Collins; Thomas R. Vigil

[57] ABSTRACT

The apparatus (10) for determining the activity of an ion (pIon) in a liquid (16) comprises a measuring circuit (10) including an ion sensitive field effect transistor (ISFET 12), a reference electrode (32) adjacent the ISFET (12), a temperature sensor (34) adjacent the ISFET (12), amplifiers (22 and 38) coupled to the ISFET (12) and temperature sensor (34), and control, computing and memory circuits (30, 44, and 46) coupled to the amplifiers and operable to maintain two of the following three parameters, $V_{gs}$ (gate-source potential), $V_{ds}$ (drain-source potential) and $I_D$ (drain-source current) at a constant value so that the third parameter can be used for determining the ion activity or pIon. The pIon sensitivity of the apparatus (10), as a function of temperature and/or the variation of the drain-source current, $I_D$, as a function of the temperature are controlled by controlling the $V_{gs}$ so that the pIon can be calculated from a formula stored in the memory (46).

4 Claims, 1 Drawing Figure

APPARATUS FOR DETERMINING THE ACTIVITY OF AN ION (PION) IN A LIQUID

BACKGROUND OF THE INVENTION

1. Field of the Invention

The present invention relates to an apparatus for determining the activity of an ion (pIon) in a liquid. The apparatus comprises a measuring circuit including an ion sensitive field effect transistor (ISFET), a reference electrode, an amplifier, a temperature sensor, a memory, and a computing circuit. The measuring circuit provides a form of temperature compensation by maintaining two of three parameters for controlling the operation of the ISFET, namely $V_{gs}$ (gate-source potential), $V_{ds}$ (drain-source potential) and $I_D$ (drain-source current) at a constant value, and the third parameter is used for determining the ion activity.

2. Description of the Prior Art

Apparatus for determining ion activity in a liquid are known in the art. For example, British patent application No. 2,077,439 describes advantages which can be obtained with the use of an ISFET for the measurement of ion activities in a liquid. However, this patent application points out that an accurate measurement of the ion activity is hampered by the fact that the gate potential and the potential of the reference electrode are affected by the temperature (i.e. differences or changes in temperature). Also the degree to which these potentials are affected by the temperature varies from ISFET to ISFET.

When taking into consideration the variation in characteristic of the ISFET and the teachings of this British patent application, as a result of change in temperature, the following equation can be obtained:

$$V = f(c) + \partial E_g/\partial T + \partial E_s/\partial T - \partial E_r/\partial T$$

in which V is the voltage measured, f(c) is the parameter to be determined, which is a function of the ion activity, and the other terms represent the variation of, respectively, the gate potential, the potential of the source relative to the gate potential, and the potential of the reference electrode with the temperature.

In utilizing this equation, the drain-source current is set at a predetermined value such that the temperature effects related to the terms given in the above equation cancel out. According to the British patent application, setting of the drain-source current at the selected value can be achieved by means of one or more series-connected fixed and variable resistors.

In a preferred embodiment of the apparatus disclosed in British patent application No. 2,077,439, the apparatus is provided with two mutually electrically coupled ISFETs to correct for changes in temperature. A correction of the pIon sensitivity with temperature is not, however, possible with this preferred embodiment.

In U.S. Pat. No. 4,267,504 it is stated that, in measuring a magnitude by means of a field effect transistor, neutralization of the temperature effect on the results of the measurement can be achieved by means of a second, temperature-sensitive element provided adjacent to the field effect transistor to obtain a separate temperature indication. At the same time, however, this patent states with regard to this feature that accurate and reliable measurement cannot be achieved in this way because it is never certain whether the two temperature-sensitive elements are always at the same temperature and whether they react to temperature variations in the same way. As will be described in greater detail hereinafter the apparatus of the present invention provides a different solution to the problem of compensating for temperature changes to obtain reliable and accurate measurements than are proposed in U.S. Pat. No. 4,267,504.

There is also proposed a scheme for temperature compensation of an ion sensing field effect transistor in German published patent application no. DE 3,144,459 which scheme is different than the temperature compensation scheme of the present invention.

As will be described in greater detail hereinafter, the present invention provides an apparatus in which the effect of the temperature on the result of an ion measurement is eliminated in a manner which is different than the temperature compensation schemes proposed in the prior art references referred to above and which is more flexible, i.e. one offering more options and better possibilities than the previously proposed temperature compensation schemes.

SUMMARY OF THE INVENTION

According to the invention, there is provided an apparatus for determining the activity of an ion (pIon) in a liquid, said apparatus comprising a measuring circuit including a field effect transistor sensitive to the ion (ISFET), a reference electrode adjacent said ISFET, a temperature sensor adjacent said ISFET, amplifying means coupled to said ISFET and to said temperature sensor, a control circuit coupled to said reference electrode and the output of said amplifying means and a computing circuit and memory coupled to said control circuit and having an output providing a temperature compensated signal indicative of ion activity, said apparatus being operable to maintain two of three parameters which control the operation of the ISFET, namely $V_{gs}$ (gate-source potential), $V_{ds}$ (drain-source potential) and $I_D$ (drain-source current) at a constant value so that the third parameter can be used for determining the ion activity or pIon, while taking into account the temperature dependent pIon sensitivity of the apparatus and compensating for the normally induced temperature dependent variations of the drain-source current $I_D$, by controlling $V_{gs}$ to hold $I_D$ fixed, while holding the drain-source potential $V_{ds}$ fixed, whereby the pIon value is calculated from the following formula stored in the memory of the apparatus:

$$pIon = pIon_{cal.} + \frac{\Delta V_{gs} + T.C. \; \Delta T}{S + (dS/dT) \; \Delta T}$$

wherein:
- $pIon_{cal.} = pIon_{calibration} =$ pIon value of the liquid at a given temperature $T_C$;
- T.C. = the variation of $V_{gs}$ with the temperature at $pIon_{cal.}$,
- S = the pIon sensitivity at the temperature $T_C$,
- (dS/dT) = the variation of the pIon sensitivity with the temperature, and
- $\Delta T$ = the difference between the actual temperature and the given temperature $T_C$.

DESCRIPTION OF THE PREFERRED EMBODIMENT

Figure 1:
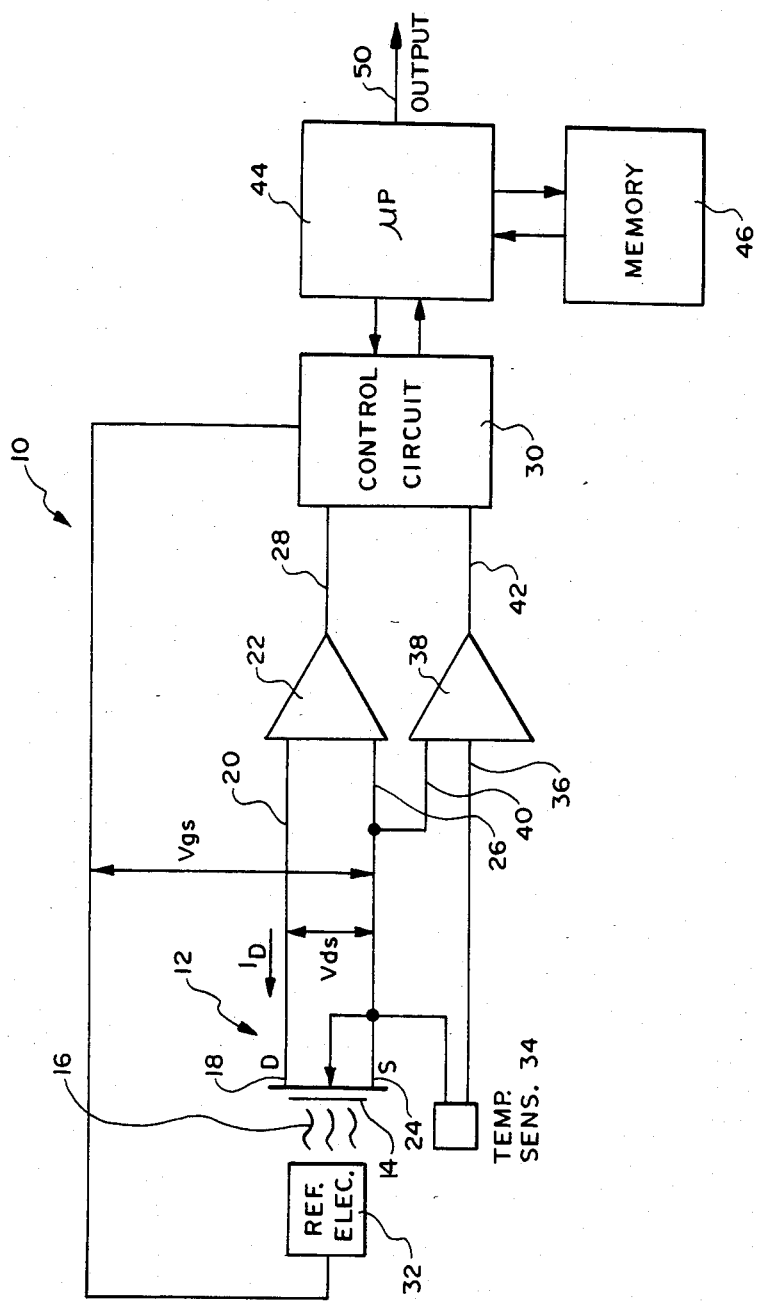
FIG. 1 is a schematic circuit diagram of the apparatus of the present invention for providing an accurate measurement of ion activity (pIon) in a liquid that is temperature independent, i.e. a temperature compensated ion measurement.

Referring now to the FIGURE, FIG. 1, there is illustrated schematically therein an apparatus 10 for determining the activity of an ion (pIon) in a liquid which apparatus 10 is constructed according to the teachings of the present invention.

The apparatus 10 includes an ion sensitive field effect transistor or ISFET 12 having a gate region 14 immersed in and exposed to a liquid 16. The ISFET 12 has a drain 18 coupled to one input 20 of an amplifier 22 and a source 24 coupled to another input 26 of the amplifier 22. An output 28 of the amplifier 22 is coupled to a control circuit 30.

A reference electrode 32 is also immersed in and exposed to the liquid 16 adjacent the gate region 14, and is coupled to the control circuit 30. According to the teachings of the present invention, a temperature sensor 34 is also immersed in the liquid 16 adjacent ISFET 12 and is coupled directly to one input 36 of an amplifier 38 and, with the source 24 of the ISFET 12, to another input 40 of the amplifier 38. An output 42 of the amplifier 38 is coupled to the control circuit 30.

The control circuit 30 is coupled to a microprocessor 44 having a memory 46 coupled thereto and having an "ion measurement" output 50.

The temperature sensed by the sensor 34 is supplied as an electrical signal to the control circuit 30, which, in conjunction with the microprocessor 44, can be used to adjust (temperature compensate) the voltage at the reference electrode 32 so that the drain current, $I_D$, is independent of temperature and temperature changes.

The scheme of the present invention is based on the insight that the temperature dependency of the operation of the ISFET 12 will be partly influenced by the effects at the interface of the pIon sensitive material and the liquid 14.

The most important parameter for describing the ion sensitivity of the apparatus 10 whose operation is based on the field effect, i.e. the flat band voltage, can be written for an ISFET as follows:

$$V_{FB} = E_r + (\phi_b - \phi)_d + ox_\chi el - \phi_{Si} - \frac{Q_{ss} + Q_{ox}}{C_{ox}}$$

where:
$E_r$ = potential of the reference electrode
$\Phi_b - \Phi_d$ = potential difference between the bulk of the liquid and the interface of the pIon sensitive material and the liquid.
$ox_\chi el$ = potential difference as a result of dipole orientation at the interface of the liquid and the pIon sensitive material.
$\Phi_{Si}$ = silicon work function
$Q_{ss}$ = fixed charge per unit area in the surface states
$Q_{ox}$ = charge in the oxide per unit area, assumed to be located at the Si/SiO$_2$ interface
$C_{ox}$ = oxide capacity per unit area. (See Bergveld and N. F. de Rooy, "The History of Chemically Sensitive Semi-Conductors", *Sensors and Actuators*, (pages 5-16) printed by El sevier Sequoia S. A. Lausanne in The Netherlands)

It can now be calculated that for a specific pH-sensitive ISFET 12 where the pIon sensitive material consists for example of Al$_2$O$_3$ (in this case, therefore, the pIon is pH), the term $$\Phi_b - \Phi_d = 2.303 \frac{RT}{F} \times \left(\frac{B'}{B'+1}\right) \times (pH_{pzc} - pH)$$

wherein:
R = gas constant
T = absolute temperature
F = Faraday constant
B' = sensibility parameter, i.e., the parameter which characterizes the pH sensibility around the pH$_{pzc}$ value: pH$_{pzc}$ = the Ph in the zero charge state (for Al$_2$O$_3$, for example, B' = 4.8).

The above relations, combined with those for the drain-source current $I_D$ (see the above article in *Sensors and Actuators* 1 (1981) (5-15) give $$I_D = B \times \left( V_{gs} - V^*_t - E_r + 2.303 \frac{RT}{F} \times \left(\frac{B'}{B'+1}\right) \times (pH_{pzc} - pH) - \frac{1}{2}V_{ds} \right) \times V_{ds} \quad (1)$$

wherein B = $\mu \times W/L \times C_{ox}$ ($\mu$ = the mobility of the charges in the inversion layer and W/L = width/length ration of the inversion layer) and $$V^*_t = V_t - E_r = 2.303 \frac{RT}{F} \times \left(\frac{B'}{B'+1}\right) \times (pH_{pzc} - pH) \text{ and}$$

$V_t$ = threshold voltage

Now, by means of the amplifiers 22 and 38, the drain-source current $I_D$ can be kept constant during variation of the pH and the temperature in the liquid by adjusting the potential $V_{gs}$, or:

$$dI_D = \left(\frac{\partial I_D}{\partial pH_T}\right) \times dpH + \left(\frac{\partial I_D}{\partial T}\right) pH \times dT = 0 \quad (2)$$

From the equations (1) and (2), the pH dependency of the potential $V_{gs}$, with a constant temperature T = T$_C$, can be derived as follows:

$$\left(\frac{dV_{gs}}{dpH}\right)_{TC} = 2.303 \frac{RT_C}{F} \times \left(\frac{B'}{B'=1}\right) - S_{TC} \quad (3)$$

wherein S$_{TC}$ represents the pH sensitivity of the apparatus 10 at the temperature T$_C$.

It can be shown that equation (3) is valid in a range of two pH units around pH$_{pzc}$. If the insulator material is, for example, Al$_2$O$_3$, whose pH$_{pzc}$ = 8, equation (3) is accordingly valid within a pH range of from 6 to 10.

The integration of (3) gives $$\Delta V_{gs}|T_C = S_{TC} \times (pH - pH_{iso}) \quad (4)$$

the meaning of pH$_{iso}$ will be explained below.

As regards the temperature dependency of the potential $V_{gs}$, the combination of equations (1) and (2) finally gives:

$$\Delta V_{gs}|pH = (dS_{TC}/dT) \times (pH - pH_{iso}) \times T \quad (5)$$

which equation applies in the temperature range around $T_C$ and in which $pH_{iso}$ is defined as the pH in the pH range from 6–10 and at a temperature around $T_C$ where the $(dV_{gs}/dT)_{pH}=0$ at a given drain-source current $I_D$.

In practice, it is now possible to correct the variation in pH sensitivity with the temperature by means of the temperature sensor 34, if the ISFET 12 is operative at the isothermal point thereof, which means that for a given $pH = pH_{iso}$ and a given reference electrode 32 the drain-source current $I_D$ can be set at a value that is independent of the temperature:

$$(dI_D/dT)_{V_{ds},V_{gs},pH_{iso}} = 0 \text{ in } I_{D.iso}$$

Means 32 is coupled to control circuit 30 through which a potential $V_{gs}$ is impressed upon the reference electrode relative to the source 24. To this potential is added a potential generated in the ion sensitive layer belonging to gate region 14 of the ISFET. The combination of these potentials influence the conductance of the channel at the surface of the substrate between source 24 and drain 18.

By modulating $V_{gs}$ it will be possible to readjust the drain current $I_D$, flowing from drain to source. For example, a change in potential as a result of the ionic activity in liquid 16 coupled with a change in $V_{gs}$ will result in $I_D$ being equal to a chosen value of $I_{Dset}$. $I_{Dset}$ is an arbitrary value of $I_D$. However, $I_{Dset}$ is best chosen to satisfy the above equation or $I_{Diso}$ for the purpose of this invention. Amplifier 22 impresses a potential $V_{gs}$ between the drain and the source, causing the drain current $I_D$ to flow between the source and a current drain of an amperage value which is determined by the value of $I_{Diso}$.

When the drain-source current $I_{D.iso}$ is kept constant by adjusting the $V_{gs}$ potential with a fixed $V_{ds}$ potential, the pH of the liquid investigated can be found from $$pH = pH_{iso} + \frac{\Delta V_{gs}}{S + (dS/dT)\Delta T}$$

If, during the measurement, the ISFET is not operative in the isothermal point, it will be necessary to correct both the variation of the pH sensitivity with the temperature (dS/dT) and the variation of the drain-source current with the temperature $(dI_D/dT)$ by means of the temperature sensor. When, by means of the amplifier, the drain-source current is kept at a fixed value, the pH of the liquid investigated can be found from $$pH = pH_{cal.} + \frac{\Delta V_{gs} + T.C.\Delta T}{S + (dS/dT)\Delta T}$$

in which $pH_{cal.}$ is the pH value at which T.C. is determined.

The drain current $I_D$ is supplied through amplifier 22 to control circuit 30 and finally to microprocessor 44 which inter-acts with control circuit 30.

Microprocessor 44 then reads out $I_{Dset}$ from the memory 46 and compares its value with the actual $I_D$. If a difference should exist, microprocessor 44 will send a signal to the control circuit 30 to readjust $V_{gs}$ so that $I_D$ is equal to $I_{Dset}$. That is to say, $dI_D$ is equal to 0 excepting short correction intervals. This relationship is set forth in its equation 2. the value of $\Delta V_{gs}$ which is needed for the readjustment of $I_D$ to $I_{Dset}$ is used to calculate the measured pIon and $\Delta V_{gs}$ is supplied to the microprocessor 44 for use in calculating that pIon value.

The actual temperature sensed by temperature sensor 34 is supplied as an electrical signal through amplifier 38 and control circuit 30 to microprocessor 44. Microprocessor 44 calculates the pIon, using the measured $\Delta V_{gs}$, and $\Delta T$ in accordance with the equation of claim 1 stored in the memory 46 and employed in microprocessor 44. The calculated pIon value is then supplied to the output 50.

Analogously to the pH, corresponding equations can be derived to calculate the activity of other ions, for example, of metal ions, such as the calculation of pK. Thus for pK the following relations can be derived:

$$pK = pK_{iso} + \frac{\Delta V_{gs}}{S + (dS/dT)\Delta T}$$

and $$pK = pK_{cal.} + \frac{\Delta V_{gs} + T.C.\Delta T}{S + (dS/dT)\Delta T}$$

The advantages of the use of the temperature sensor 34 in the apparatus 10 according to the invention can be summarized as follows:

(a) the temperature sensor 34 permits correcting the variation in pIon sensitivity with the temperature, if the apparatus 10 is operative at the isothermal point thereof;

(b) the temperature sensor 34 permits correcting both the variation in pIon sensitivity with the temperature and the variation in drain-source current with the temperature, if the measurement is actually carried out incorrectly if the apparatus 10 is not operative at the isothermal point, and (c) the isothermal point in which $I_D = I_{D.iso}$ can be varied by varying the pIon of the liquid at which the determination is carried out and/or by changing the reference electrode 32 of the apparatus 10.

It will be understood that from the equations (e.g. equation (1), (2), (3), (4) and/or (5)), stored in the memory 46, the microprocessor 44, utilizing those equations and signal values received from the control circuit 30 can adjust the voltage of the reference electrode 32 or the drain-source current $I_D$ to obtain an accurate measurement of ion activity.

From the foregoing description, it will be apparent that the apparatus 10 of the present invention and the method for using same described above have a number of advantages some of which have been described above and others of which are inherent in the invention. In particular, the apparatus 10 and method for using same provide an accurate, simple and flexible means for providing a temperature compensated measurement of ion activity in a measuring apparatus including an ISFET.

Also from the foregoing description, it will be apparent that modifications can be made to the apparatus 10 and method for using same without departing from the teachings of the present invention. Accordingly, the scope of the invention is only to be limited as necessitated by the accompanying claims.

We claim:

1. An apparatus for determining the activity of an ion (pIon) in a liquid, said apparatus comprising a measuring circuit including a field effect transistor sensitive to the ion (ISFET), a reference electrode adjacent said ISFET, a temperature sensor adjacent said ISFET, amplifying means coupled to said ISFET and to said temperature sensor, a control circuit coupled to said reference electrode and the output of said amplifying means and a computing circuit and memory coupled to said control circuit and having an output providing a temperature compensated signal indicative of ion activity, said apparatus being operable to maintain two of three parameters which control the operation of the ISFET, namely $V_{gs}$ (gate-source potential), $V_{ds}$ (drain-source potential) and $I_D$ (drain-source current) at a constant value so that the third parameter can be used for determining the ion activity or pIon, while taking into account the temperature dependent pIon sensitivity of the apparatus and compensating for the normally induced temperature dependent variations of the drain-source current, $I_D$, by controlling $V_{gs}$ to hold $I_D$ fixed, while holding the drain-source potential $V_{ds}$ fixed, whereby the pIon value is calculated from the following formula stored in the memory of the apparatus:

$$pIon = pIon_{cal.} + \frac{\Delta V_{gs} + T.C. \Delta T}{S + (dS/dT) \Delta T}$$

wherein:
- $pIon_{cal.} = pIon_{calibration} = $ pIon value of the liquid at a given temperature $T_C$;
- T.C. = the variation of $V_{gs}$ with the temperature at $pIon_{cal.}$,
- S = the pIon sensitivity at the temperature $T_C$,
- (dS/dT) = the variation of the pIon sensitivity with the temperature, and
- $\Delta T$ = the difference between the actual temperature and the given temperature $T_C$.

2. The apparatus according to claim 1, characterized in that the circuits are constructed, connected and arranged so that the drain-source current $I_D$ is adjustable to a value $I_{D.iso}$ in which $((dI_D/dT))_{Vds,Vgs,pHiso}=0$ and the pIon sensitivity of the apparatus as a function of the temperature is corrected by controlling $V_{gs}$, while the pIon is calculated from the formula stored in said memory $$pIon = pIon_{iso} = \frac{\Delta V_{gs}}{S + (dS/dT)\Delta T}$$

wherein: $pIon_{iso}$ is that value of the pIon, within a series of pIon values depending on the pIon sensitive material used in the ISFET and at a temperature around the given temperature $T_C$, at which $((dV_{gs})/(dT))_{pIon}=0$ for the value of the drain-source $I_{D.iso}$.

3. A method for determining the activity of an ion in a liquid using an apparatus including an ISFET immersed in a liquid with a reference electrode and a temperature sensor, said method comprising the steps of: sensing the gate-source potential $V_{gs}$; sensing the drain-source potential $V_{ds}$; sensing the drain-source current $I_D$; maintaining two of the three parameters $V_{gs}$, $V_{ds}$ or $I_D$ at a constant value while taking into account the temperature dependent pIon sensitivity of the apparatus and compensating for the normally induced temperature dependent variations of the drain-source current $I_D$; controlling $V_{gs}$ to hold $I_D$ fixed, while holding the drain-source potential $V_{ds}$ fixed; and calculating the pIon using the formula:

$$pIon = pIon_{cal.} + \frac{\Delta V_{gs} + T.C.\Delta T}{D + (dS/dT)\Delta T}$$

wherein:
- $pIon_{cal.} = pIon_{calibration} = $ pIon value of the liquid at a given temperature $T_C$;
- T.C. = the variation of $V_{gs}$ with the temperature at $pIon_{cal.}$,
- S = the pIon sensitivity at the temperature $T_C$,
- (dS/dT) = the variation of the pIon sensitivity with the temperature, and
- T = the difference between the actual temperature and the given temperature $T_C$.

4. The method of claim 3 characterized by including the steps of: adjusting the drain-source current to a value:

$$I_{D.iso}$$

in which $((dI_D/dT))_{Vds,Vgs,pHiso}=0$; controlling $V_{gs}$ to correct the pIon sensitivity of the apparatus as a function of the temperature; and calculating the pIon using the formula:

$$pIon = pIon_{iso} = \frac{\Delta V_{gs}}{S + (dS/DT)\Delta T}$$

wherein: $pIon_{iso}$ is that value of the pIon, within a series of pIon values depending on the pIon sensitive material used in the ISFET and at a temperature around the given temperature $T_C$, at which $((dV_{gs})/(dT))_{pIon}=0$ for the value of the drain-source $I_{D.iso}$.

* * * * *